United States Patent

Schuetz et al.

Patent Number: 5,166,216
Date of Patent: Nov. 24, 1992

[54] METHYL α-ARYLACRYLATES SUBSTITUTED BY A HETEROCYCLIC RADICAL AND THEIR USE

[75] Inventors: Franz Schuetz, Ludwigshafen; Hans-Juergen Neubauer, Muenster-Hiltrup; Thomas Kuekenhoehner, Frankenthal; Ulrich Schirmer, Heidelberg; Peter Hofmeister, Neustadt; Christoph Kuenast, Otterstadt; Eberhard Ammermann, Ludwigshafen; Gisela Lorenz, Neustadt; Uwe Kardorff, Mannheim, all of Fed. Rep. of Germany

[73] Assignee: BASF Aktiengesellschaft, Ludwigshafen, Fed. Rep. of Germany

[21] Appl. No.: 701,019

[22] Filed: May 13, 1991

Related U.S. Application Data

[63] Continuation of Ser. No. 418,664, Oct. 10, 1989, abandoned.

[30] Foreign Application Priority Data

Oct. 27, 1988 [DE] Fed. Rep. of Germany ....... 3836581

[51] Int. Cl.[5] .................... C07D 231/12; A01N 43/56

[52] U.S. Cl. .................... 514/406; 548/128; 548/131; 548/136; 548/143; 548/204; 548/214; 548/236; 548/247; 548/268.4; 548/268.6; 548/562; 548/377.1; 548/373.1; 548/376.1; 548/342.5; 548/343.5; 549/79; 549/501

[58] Field of Search .......... 514/406; 548/378

[56] References Cited

FOREIGN PATENT DOCUMENTS 178826 4/1986 European Pat. Off. .......... 548/378
256667 2/1988 European Pat. Off. .

Primary Examiner—Robert Gerstl
Attorney, Agent, or Firm—Oblon, Spivak, McClelland, Maier & Neustadt

[57] ABSTRACT

Methyl α-arylacrylates substituted by a heterocyclic radical and having the general formula

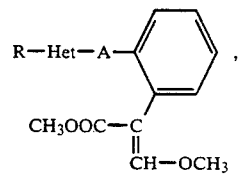

(I)

where R is alkyl, alkenyl, haloalkyl, cycloalkyl, alkoxy, alkylcarbonyl, alkoxycarbonyl, halogen or aryl, the aromatic ring being unsubstituted or substituted, Het is a five-membered heteroaromatic ring which is unsubstituted or substituted and has from one to three heteroatoms, and A is ethenylene, ethylene, methyleneoxy or methylenethio, and fungicides and pesticides containing these compounds.

7 Claims, No Drawings

METHYL α-ARYLACRYLATES SUBSTITUTED BY A HETEROCYCLIC RADICAL AND THEIR USE

This application is a continuation of application Ser. No. 07/418,664, filed on Oct. 10, 1989, now abandoned.

The present invention relates to useful novel methyl α-arylacrylates substituted by a heterocyclic radical, which have a fungicidal and insecticidal action, and fungicides and insecticides which contain these compounds.

It is known that methyl acrylates, for example methylα-[2-(benzoxazol-2'-yloxy)-phenyl]-β-methoxyacrylate (EP-256,667) can be used as insecticides. However, its insecticidal action is unsatisfactory.

We have found that methyl α-arylacrylates substituted by a heterocyclic radical, of the general formula

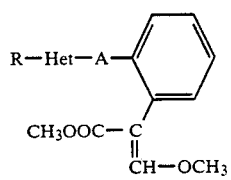

(I)

where R is $C_1$-$C_8$-alkyl, $C_2$-$C_8$-alkenyl, $C_1$-$C_4$-haloalkyl, $C_3$-$C_6$-cycloalkyl, $C_1$-$C_4$-alkoxy, $C_1$-$C_4$-alkylcarbonyl, $C_1$-$C_4$-alkoxycarbonyl, halogen or aryl, the aromatic ring being unsubstituted or substituted by $C_1$-$C_8$-alkyl, $C_3$-$C_6$-cycloalkyl, $C_1$- or $C_2$-haloalkyl, $C_1$-$C_4$-alkoxy, halogen, cyano or nitro, Het is a five-membered heteroaromatic ring which is unsubstituted or substituted by methyl at a nitrogen atom and has from 1 to 3 heteroatoms, such as oxygen, sulfo or nitrogen, and is bonded to A via a carbon atom and A is ethenylene, ethylene, methyleneoxy or methylenethio, have an excellent fungicidal and insecticidal action, which is better than that of the known methyl acrylates.

The radicals mentioned in the general formula may have, for example, the following meanings:

R may be, for example, $C_1$-$C_8$-alkyl, in particular $C_1$-$C_4$-alkyl (e.g. methyl, ethyl, n-propyl, isopropyl, n-butyl, isobutyl, sec-butyl, tert-butyl, n-pentyl, isopentyl, sec-pentyl, tert-pentyl, neopentyl, hexyl, heptyl or octyl), $C_2$-$C_8$-alkenyl, in particular $C_2$- or $C_3$-alkenyl (e.g. vinyl, allyl, propenyl or isopropenyl), $C_1$-$C_4$-haloalkyl (e.g. trifluoromethyl, 2,2,2-trifluoroethyl, pentafluoroethyl, chloromethyl, dichloromethyl or trichloromethyl), $C_3$-$C_6$-cycloalkyl (e.g. cyclopropyl, cyclobutyl, cyclopentyl or cyclohexyl), $C_1$-$C_4$-alkoxy (e.g. methoxy, ethoxy, n-propoxy, isopropoxy, n-butoxy, isobutoxy, secbutoxy or tert-butoxy), $C_1$-$C_4$-alkylcarbonyl (e.g. acetyl, propanoyl, butanoyl, pentanoyl), $C_1$-$C_4$-alkoxycarbonyl (e.g. methoxycarbonyl, ethoxycarbonyl, propoxycarbonyl or butoxycarbonyl), halogen (e.g. fluorine, chlorine or bromine), or aryl (e.g. phenyl), and the aromatic ring may be unsubstituted or substituted by one to three of the following radicals:

$C_1$-$C_8$-alkyl, in particular $C_1$-$C_4$-alkyl (e.g. methyl, ethyl, n-propyl, isopropyl, n-butyl, isobutyl, sec-butyl, tert-butyl, n-pentyl, isopentyl, sec-pentyl, tert-pentyl, neopentyl, hexyl, heptyl or octyl), $C_3$-$C_6$-cycloalkyl (e.g. cyclopropyl, cyclobutyl, cyclopentyl or cyclohexyl), $C_1$- or $C_2$-haloalkyl (e.g. trifluoromethyl, 2,2,2-trifluoroethyl, pentafluoroethyl, chloromethyl, dichloromethyl or trichloromethyl), $C_1$-$C_4$-alkoxy (e.g. methoxy, ethoxy, propoxy or butoxy), halogen (e.g. fluorine, chlorine or bromine), cyano or nitro.

Het may be, for example, a five-membered heteroaromatic ring which is unsubstituted or substituted by methyl at a nitrogen atom and has 1 to 3 heteroatoms, such as oxygen, sulfur or nitrogen (e.g. pyrrolyl, furyl, thienyl, pyrazolyl, imidazolyl, 1,2,4-triazolyl, oxazolyl, N-methylpyrazolyl, thiazolyl, isoxazolyl, isothiazolyl, 1,3,4-oxadiazolyl, 1-N-methyl-1,2,4-triazolyl, 1,3,4-thiadiazolyl, 1,2,4-oxadiazolyl or 1,2,4-thiadiazolyl), and is bonded to A via a carbon atom.

A may be, for example, ethenylene (—CH=CH—), ethylene (—$CH_2$—$CH_2$—), methyleneoxy (—$CH_2$—O—) or methylenethio (—$CH_2$—S—).

The novel compounds can be prepared, for example, by the following processes:

The compounds of the general formula I a (where R and Het have the abovementioned meanings and A is ethenylene) and of the general formula I b (R and Het have the abovementioned meanings and A is methyleneoxy) are obtained from the methyl α-aryl-β-hydroxyacrylate derivatives of the general formula V which are substituted by a heterocyclic radical and which may occur in equilibrium with the formyl derivatives VI, by reaction with an alkylating agent (e.g. dimethyl sulfate or methyl iodide) in the presence of a base (e.g. potassium carbonate or sodium carbonate) in a diluent (e.g. acetone). In the formulae below, L is a leaving group (e.g. methylsulfate or iodide).

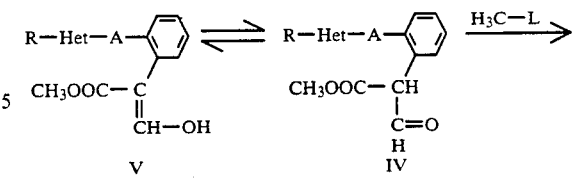

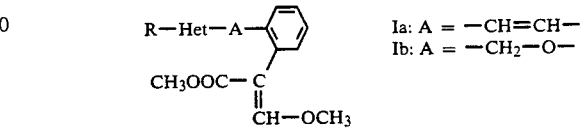

Ia: A = —CH=CH—
Ib: A = —$CH_2$—O—

The heterocyclic methyl α-aryl-β-hydroxyacrylates of the general formula V where A is ethenylene or methyleneoxy are obtained from methyl phenylacetates of the general formula II which are substituted by a heterocyclic radical by reaction with methyl formate using a base (e.g. sodium hydride, lithium diisopropylamide or sodium methylate) in an inert solvent, e.g. diethyl ether or tetrahydrofuran (cf. Ann. Chem. 424 (1921), 214).

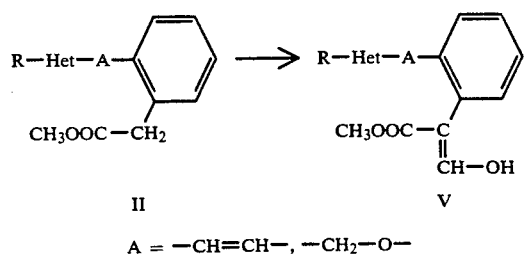

A = —CH=CH—, —$CH_2$—O—

The methyl phenylacetates IIa (A=ethenylene) which are substituted by a heterocyclic radical and are required as starting compounds are prepared by reacting a methyl 2-formylphenylacetate III with a methanephosphonic ester of the general formula IV (where R and Het have the abovementioned meanings and $R^1$ is methyl or ethyl). The reaction is carried out in a conventional manner (cf. for example J. Am. Chem. Soc. 83 (1961), 1733). The starting materials are usually used in a stoichiometric ratio. An excess of up to 10% by weight of one of the two reactants over and above the stoichiometric amounts is possible. The reaction is advantageously carried out in an inert solvent or diluent (e.g. diethyl ether, tetrahydrofuran, methyl tert-butyl ether, ethylene glycol dimethyl ether, toluene or dimethyl sulfoxide) in the presence of an equivalent amount of a base (e.g. sodium hydride, sodium amide, potassium tert-butylate, sodium methylate, butyllithium, phenyllithium, sodium bis-trimethylsilylamide or methylsulfinylmethylsodium). The reactions usually take place at from $-70°$ to $+30°$ C. Since they take place with evolution of heat in some cases, it may be advantageous to provide a means of cooling.

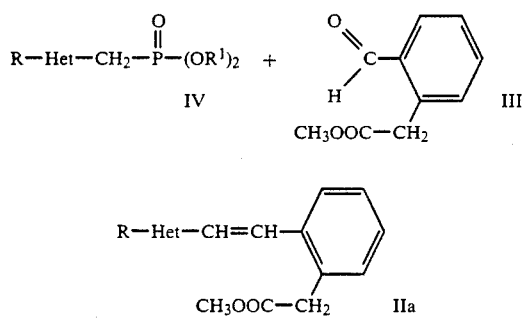

Methyl 2-formylphenylacetate III is obtained by esterifying 2-formylphenylacetic acid VII with methanol under standard conditions. 2-Formylphenylacetic acid VII is prepared in a simple manner by ozonolysis of the trimethylsilyl enol ether VIII of 2-indanone IX (Tetrahedron Lett. 25 (1984), 3659; Tetrahedron 43 (1987), 2075).

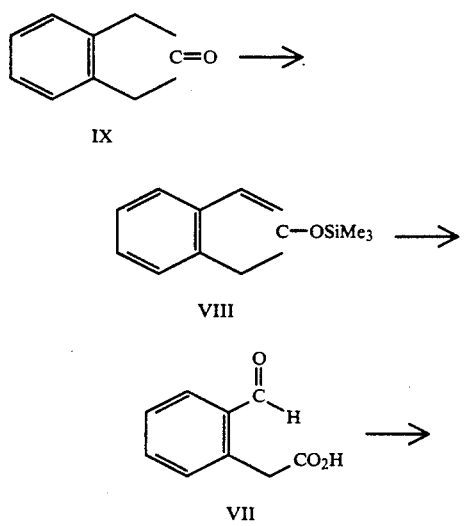

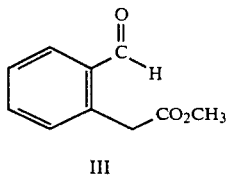

The methanephosphonic esters substituted by a heterocyclic radical, of the general formula IV (where R and Het have the abovementioned meanings and $R^1$ is methyl or ethyl) are obtained by reacting a methylhalogen compound X which contains a five-membered heteroaromatic ring and is of the general formula R—Het—$CH_2$—Z (where Z is chlorine or bromine) with trimethyl phosphite or triethyl phosphite $P(OR^1)_3$ (cf. Methoden der organischen Chemie, Volume 12/1, page 443, Thieme, Stuttgart 1963).

The methyl phenylacetates II b substituted by a heterocyclic radical (A=methyleneoxy), which are required as starting compounds, are prepared by reacting a methylhalogen compound X containing a five-membered heteroaromatic ring (X=chlorine or bromine) with methyl ortho-hydroxyphenylacetate XI.

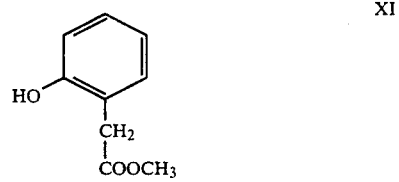

The reaction can be carried out by a procedure in which stoichiometric amounts of the starting compounds X and XI in an inert solvent or diluent (e.g. acetone, acetonitrile, dimethyl sulfoxide, dioxane, dimethylformamide, N-methylpyrrolidone, N,N'-dimethylpropyleneurea or pyridine) are reacted with the addition of an equivalent amount of a base (e.g. sodium carbonate or potassium carbonate).

In an alternative procedure, the methyl orthohydroxyphenylacetate XI can first be converted with a base (e.g. sodium hydroxide or potassium hydroxide) into the corresponding sodium or potassium phenolate and the latter then reacted, in an inert solvent or diluent (e.g. dimethylformamide), with the methylhalogen compound X containing a five-membered heteroaromatic ring to give the methyl phenylacetates II b substituted by heterocyclic radicals.

A second process is available for the preparation of the novel compounds of the general formula I a (where R and Het have the abovementioned meanings and A is ethenylene). In this process, an aldehyde which contains a five-membered heteroaromatic ring and is of the general formula XII (where R and Het have the abovementioned meanings) is reacted with dimethyl 2-($\beta$-methoxy-$\alpha$-methoxycarbonylvinyl)-benzylphosphonate XIII (cf. J. Am. Chem. Soc. 83 (1961), 1733).

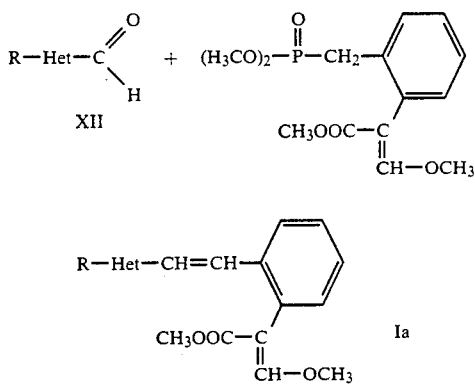

Dimethyl 2-(β-methoxy-α-methoxycarbonylvinyl)-benzylphosphonate XIII is disclosed in DE-3 519 280 and DE-3 545 318.

The novel compounds of the general formula I c (where R and Het have the abovementioned meanings and A is ethylene) are obtained by selective reduction of the novel compounds of the general formula I a (where R and Het have the abovementioned meanings and A is ethyenylene). The reduction is usually carried out catalytically with hydrogen (cf. Methoden der organischen Chemie, Volume 5/2 b, page 264, Thieme, Stuttgart 1981).

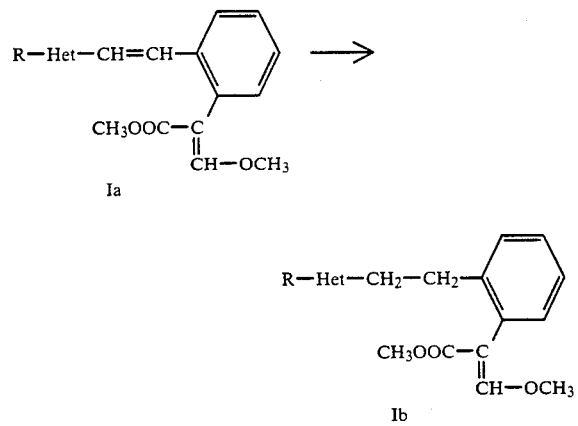

For the preparation of the novel compounds of the general formula I as claimed in claim 1 by the process described above, methylhalogen compounds X containing a five-membered heteroaromatic ring and aldehydes XII containing a five-membered heteroaromatic ring are required as educts. These compounds are either known or can be prepared by known processes. Appropriate preparation processes are described in, for example, J. Chem. Soc. (C), 1970, 2563; Synth. Commun. 13 (1983), 741; J. Org. Chem. 50 (1985), 5272; Acta Chem. Scand. 24 (1970), 99; Acta Chem. Scand. 26 (1972), 1851; J. Chem. Soc. 1961, 2733; Liebigs Ann. Chem. 1985, 1377; J. Heterocyclic Chem. 23 (1986), 1535; Synthesis 1982, 318; Eur. J. Med. Chem. 19 (1984), 285; Chem. Pharm. Bull. 34 (1986), 2840; Liebigs Ann. Chem. 717 (1968), 148; Heterocycles 26 (1987), 947; Tetrahedron 43 (1987), 235; J. Chem. Soc., Perkin Trans. I, 1976, 570; Chem. Ber. 106 (1973), 3345; J. Org. Chem. 43 (1978), 3736; J. Org. Chem. 43 (1978), 3742; J. Indian Chem. Soc. 64 (1987), 314; Chem. Ber. 121 (1988), 723; DE-3118258; Chem. Ber. 101 (1968), 3872.

The novel compounds of the general formula I as claimed in claim 1 may occur as E or Z isomers at the double bonds (methyl β-methoxyacrylate group and side chain for A=ethenylene). The stereoisomers can be separated, for example, by column chromatography or isolated in pure form on the basis of their solubility differences. The pure isomers can be converted into one another by known methods. The pure isomeric compounds and their mixtures are embraced by the present invention. Regarding the use of the novel compounds as fungicides and insecticides, both the diastereomer mixtures and the pure isomeric compounds as well as their mixtures obtained in the synthesis are suitable.

The Examples which follow illustrate the synthesis of the novel compounds.

EXAMPLE 1

Methyl alpha-2-[2'-(3''-cyclopropylisoxazol-5''-yl)-ethen-1'-yl]-phenyl-β-methoxyacrylate

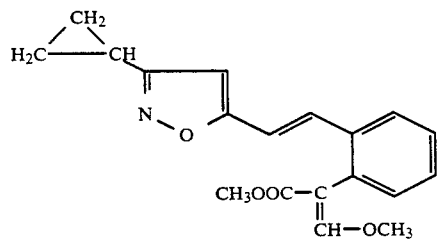

a) 30.3 g (0.30 mole) of triethylamine are added to a solution of 36.5 g (0.28 mole) of 2-indanone and 32.4 g (0.30 mole) of trimethylchlorosilane in 300 ml of tetrahydrofuran at room temperature while stirring. Stirring is continued for a further 3 hours at room temperature (20° C.), the precipitate which has separated out is filtered off under suction and the filtrate is evaporated down. The residue is purified by distillation (53° C., 0.3 mbar). 40.6 g (72%) of 2-trimethylsilyloxy-1H-indene are obtained as a colorless liquid in this manner.

b) 40.0 g (0.20 mole) of 2-trimethylsilyloxy-1H-indene are dissolved in a mixture of 500 ml of methanol and 150 ml of methylene chloride, and 14.0 g (0.30 mole) of ozone are added in the course of 5 hours at −70° C. After removal of excess ozone with nitrogen, 150 ml (2.0 moles) of dimethyl sulfide are added and the mixture is stirred overnight at room temperature. Thereafter, the solution is evaporated down and the residue is taken up in NaHCO₃ solution. The aqueous phase is washed with diethyl ether and brought to pH 2 with dilute HCl. The mixture is then extracted with diethyl ether and the combined organic phases are dried over MgSO₄ and evaporated down. 24.1 g (75%) of 2-formylphenylacetate are obtained in the form of colorless crystals (mp.: 103°–105° C.).

c) 24.0 g (0.15 mole) of 2-formylphenylacetic acid and 0.1 g of p-toluenesulfonic acid in 250 ml of methanol are refluxed for 2 hours. Thereafter, the solution is evaporated down, the residue is taken up in diethyl ether and the solution is washed with dilute HCl. The organic phase is separated off, dried over MgSO₄ and evaporated down. The residue is purified by distillation (90° C., 0.4 mbar). 19.3 g (74%) of methyl 2-formylphenylacetate are obtained as a colorless liquid in this manner.

d) 43.3 ml of a 1.5 molar solution of n-butyllithium in hexane (0.065 millimole) are added dropwise to a solution of 15.6 g (0.06 mole) of diethyl 3-cyclopropylisoxazol-5-ylmethanephosphonate in 50 ml of tetrahydrofuran at 20° C. The mixture is stirred for 20 minutes at 20° C., after which a solution of 10.7 g (0.06 mole) of methyl 2-formylphenylacetate in tetrahydrofuran is added dropwise at this temperature. The reaction mixture is stirred overnight, poured onto ice water and extracted with methyl tert-butyl ether. The organic phases are washed with water, dried over MgSO$_4$ and evaporated down. The residue is chromatographed over silica gel (8:2 cyclohexane/ethyl acetate). 8.0 g (47%) of methyl 2-[2'-(3''-cyclopropylisoxazol-5''-yl)-ethen-1'-yl]-phenylacetate are obtained as a colorless oil.

$^1$H-NMR (CDCl$_3$): 0.87 (m, 2H); 1.03 (m, 2H); 3.68 (s, 3H); 3.77 (s, 2H); 5.93 (s, 1H); 6.80 (d, 1H); 7.25–7.62 (m, 4H); 7.52 (d, 1H).

e) A mixture of 6.0 g (0.02 mole) of methyl 2-[2'-(3''-cyclopropylisoxazol-5''-yl)-ethen-1'-yl]-phenylacetate, 2.8 g (0.05 mole) of methyl formate and 50 ml of diethyl ether is added dropwise to a suspension of 0.76 g (0.03 mole) of sodium hydride in 30 ml of diethyl ether at room temperature. The mixture is stirred for 12 hours at room temperature, after which hydrolysis is carried out with ice water. The aqueous phase is brought to pH 4 with dilute HCl and extracted with diethyl ether. The combined ether phases are dried over MgSO$_4$ and evaporated down. 5.4 g (82%) of methyl alpha-2-[2'-(3''-cyclopropylisoxazol-5''-yl)-ethen-1'-yl]-phenyl-$\beta$-hydroxyacrylate are obtained as a colorless oil.

f) 5.4 g (0.02 mole) of the methyl acrylate obtained under e), 2.4 g (0.02 mole) of potassium carbonate and 2.2 g (0.02 mole) of dimethyl sulfate in 60 ml of acetone are stirred for 12 hours at room temperature. Thereafter, the solution is filtered off from the precipitate, the filtrate is evaporated down and the residue is taken up in diethyl ether. The organic phase is washed with dilute NH$_4$OH solution, dried over MgSO$_4$ and evaporated down. The residue is purified by chromatography over silica gel (8:2 cyclohexane/ethyl acetate). The oil obtained is covered with a layer of diisopropyl ether and is crystallized by trituration. 4.5 g (80%) of methyl $\alpha$-2-[2'-(3''-cyclopropylisoxazol-5''-yl)-ethen-1'-yl]-phenyl-$\beta$-methoxyacrylate are obtained in the form of colorless crystals (mp.: 109°–111° C., compound No. 122).

EXAMPLE 2

Methyl alpha-2-[2'-(N-para-chlorophenylpyrrol-3''-yl)-ethen-1'-yl]-phenyl-$\beta$-methoxyacrylate

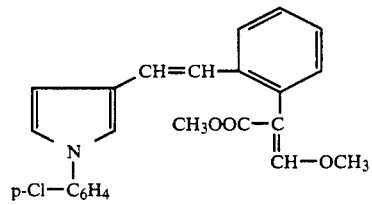

A solution of 13.7 g (0.04 mole) of dimethyl 2-($\beta$-methoxy-$\alpha$-methoxycarbonylvinyl)-benzylphosphonate and 9.0 g (0.04 mole) of N-para-chlorophenyl-pyrrol-3-yl-carboxaldehyde in 100 ml of dimethylformamide is added dropwise to a suspension of 1.1 g (0.04 mole) of sodium hydride in 50 ml of dimethylformamide at 0° C., while stirring. Stirring is continued for a further hour at 0° C. and for 12 hours at room temperature. Thereafter, the mixture is hydrolyzed with ice water and extracted with diethyl ether. The organic phase is dried over MgSO$_4$. On evaporation of the ether phase, crystallization begins. 5.4 g (31%) of the title compound were obtained in the form of colorless crystals in this manner (mp.: 146°–147° C., compound No. 8).

EXAMPLE 3

Methyl alpha-2-[2'-(N-para-chlorophenylpyrrol-3''-yl)-eth-1'-yl]-phenyl-$\beta$-methoxyacrylate 4.2 g (0.01 mole) of methyl alpha-2-[2'-(N-para-chlorophenylpyrrol-3''-yl)-ethen-1'-yl]-phenyl-$\beta$-methoxyacrylate (cf. Example 2) are dissolved in 100 ml of tetrahydrofuran and hydrogenated in the presence of 1.0 g of Pd/C (10% strength) under 0.05 bar hydrogen gage pressure and at 0° C. After the absorption of 220 ml of hydrogen, the mixture is filtered and the organic phase is evaporated down. The residue is chromatographed over silica gel (toluene). The oil obtained is covered with a layer of diisopropyl ether and crystallized by trituration. 1.9 g (45%) of the title compound are obtained in the form of colorless crystals (mp.: 115°–116° C., compound No. 14).

The following compounds can be prepared in a similar manner:

TABLE 1

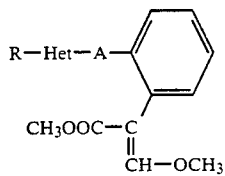

(I)

Compounds of the general formula I.
The first configuration statement refers to the methyl β-methoxyacrylate group, and the second to the ethenylene group in the compounds of the general formula I a (A = ethenylene).

| No. | R | Position of R on Het | Het—A— | mp.: (°C.) (Isomer) |
|---|---|---|---|---|
| 1 | C₆H₅ | 1 | pyrrol-2-yl—CH=CH— | |
| 2 | 4-Cl—C₆H₄ | 1 | pyrrol-2-yl—CH=CH— | |
| 3 | C₆H₅ | 1 | pyrrol-2-yl—CH₂—CH₂— | |
| 4 | 4-Cl—C₆H₄ | 1 | pyrrol-2-yl—CH₂—CH₂— | |
| 5 | C₆H₅ | 1 | pyrrol-2-yl—CH₂—O— | |
| 6 | 4-Cl—C₆H₄ | 1 | pyrrol-2-yl—CH₂—O— | |
| 7 | C₆H₅ | 1 | pyrrol-3-yl—CH=CH— | 133–135 (E, E) |
| 8 | 4-Cl—C₆H₅ | 1 | pyrrol-3-yl—CH=CH— | 146–147 (E, E) |
| 9 | 4-Br—C₆H₅ | 1 | pyrrol-3-yl—CH=CH— | |
| 10 | 4-OCH₃—C₆H₄ | 1 | pyrrol-3-yl—CH=CH— | |
| 11 | 4-NO₂—C₆H₄ | 1 | pyrrol-3-yl—CH=CH— | 142–143 (E, E) |

TABLE 1-continued

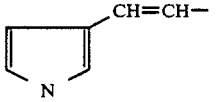

Compounds of the general formula I.
The first configuration statement refers to the methyl β-methoxyacrylate group, and the second to the ethenylene group in the compounds of the general formula I a (A = ethenylene).

| No. | R | Position of R on Het | Het—A— | mp.: (°C.) (Isomer) |
|---|---|---|---|---|
| 12 | 2,6-(CH$_3$)$_2$—C$_6$H$_3$ | 1 | 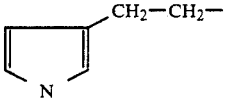 CH=CH— | |
| 13 | C$_6$H$_5$ | 1 | 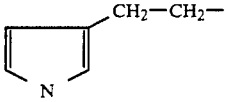 CH$_2$—CH$_2$— | |
| 14 | 4-Cl—C$_6$H$_4$ | 1 | 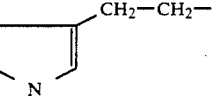 CH$_2$—CH$_2$— | 115–116 (E) |
| 15 | 4-Br—C$_6$H$_4$ | 1 | 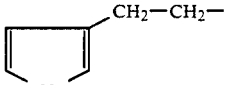 CH$_2$—CH$_2$— | |
| 16 | 4-OCH$_3$—C$_6$H$_4$ | 1 | 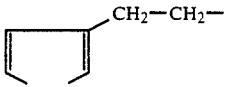 CH$_2$—CH$_2$— | |
| 17 | 4-NO$_2$—C$_6$H$_4$ | 1 | 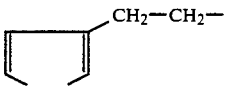 CH$_2$—CH$_2$— | |
| 18 | 2,6-(CH$_3$)$_2$—C$_6$H$_3$ | 1 | 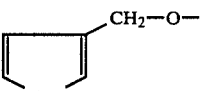 CH$_2$—CH$_2$— | |
| 19 | C$_6$H$_5$ | 1. | 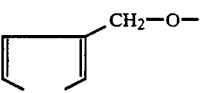 CH$_2$—O— | |
| 20 | 4-Cl—C$_6$H$_4$ | 1 | 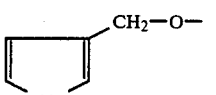 CH$_2$—O— | |
| 21 | 4-Br—C$_6$H$_4$ | 1 | 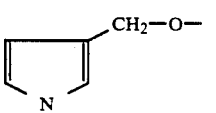 CH$_2$—O— | |
| 22 | 4-OCH$_3$—C$_6$H$_4$ | 1 | CH$_2$—O— | |

TABLE 1-continued

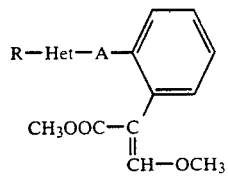
(I)

Compounds of the general formula I.
The first configuration statement refers to the methyl β-methoxyacrylate group, and the second to the ethenylene group in the compounds of the general formula I a (A = ethenylene).

| No. | R | Position of R on Het | Het—A— | mp.: (°C.) (Isomer) |
|-----|---|---------------------|--------|---------------------|
| 23 | 4-NO$_2$—C$_6$H$_4$ | 1 | pyrrole-CH$_2$—O— | |
| 24 | 2,6-(CH$_3$)$_2$—C$_6$H$_3$ | 1 | pyrrole-CH$_2$—O— | |
| 25 | (CH$_3$)$_2$CH | 5 | furan-CH=CH— | |
| 26 | cyclo-C$_3$H$_5$ | 5 | furan-CH=CH— | |
| 27 | 4-Cl—C$_6$H$_4$ | 5 | furan-CH=CH— | |
| 28 | 4-OCH$_3$—C$_6$H$_4$ | 5 | furan-CH=CH— | |
| 29 | (CH$_3$)$_2$CH | 5 | furan-CH$_2$—CH$_2$ | |
| 30 | cyclo-C$_3$H$_5$ | 5 | furan-CH$_2$—CH$_2$ | |
| 31 | 4-Cl—C$_6$H$_5$ | 5 | furan-CH$_2$—CH$_2$ | |
| 32 | 4-OCH$_3$—C$_6$H$_5$ | 5 | furan-CH$_2$—CH$_2$ | |
| 33 | (CH$_3$)$_2$CH | 5 | furan-CH$_2$—O— | |
| 34 | cyclo-C$_3$H$_5$ | 5 | furan-CH$_2$—O— | |

TABLE 1-continued

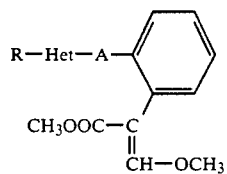
(I)

Compounds of the general formula I.
The first configuration statement refers to the methyl β-methoxyacrylate group, and the second to the ethenylene group in the compounds of the general formula I a (A = ethenylene).

| No. | R | Position of R on Het | Het—A— | mp.: (°C.) (Isomer) |
|-----|---|---------------------|--------|---------------------|
| 35 | 4-Cl—C$_6$H$_4$ | 5 | furan-CH$_2$—O— | |
| 36 | 4-OCH$_3$—C$_6$H$_4$ | 5 | furan-CH$_2$—O— | |
| 37 | (CH$_3$)$_2$CH | 4 | furan-CH=CH— | |
| 38 | cyclo-C$_3$H$_5$ | 4 | furan-CH=CH— | |
| 39 | 4-Cl—C$_6$H$_4$ | 4 | furan-CH=CH— | |
| 40 | 4-OCH$_3$—C$_6$H$_4$ | 4 | furan-CH=CH— | |
| 41 | (CH$_3$)$_2$CH | 4 | furan-CH$_2$—CH$_2$ | |
| 42 | cyclo-C$_3$H$_5$ | 4 | furan-CH$_2$—CH$_2$ | |
| 43 | 4-Cl—C$_6$H$_4$ | 4 | furan-CH$_2$—CH$_2$ | |
| 44 | 4-OCH$_3$—C$_6$H$_4$ | 4 | furan-CH$_2$—CH$_2$ | |
| 45 | (CH$_3$)$_2$CH | 4 | furan-CH$_2$—O— | |
| 46 | cyclo-C$_3$H$_5$ | 4 | furan-CH$_2$—O— | |

TABLE 1-continued $$\text{R—Het—A—} \underset{\underset{\text{CH—OCH}_3}{\|}}{\underset{\text{CH}_3\text{OOC—C}}{\bigcirc}} \quad (I)$$

Compounds of the general formula I.
The first configuration statement refers to the methyl β-methoxyacrylate group, and the second to the ethenylene group in the compounds of the general formula I a (A = ethenylene).

| No. | R | Position of R on Het | Het—A— | mp.: (°C.) (Isomer) |
|---|---|---|---|---|
| 47 | 4-Cl—C$_6$H$_4$ | 4 | furan-2-yl-CH$_2$—O— | |
| 48 | 4-OCH$_3$—C$_6$H$_4$ | 4 | furan-2-yl-CH$_2$—O— | |
| 49 | (CH$_3$)$_2$CH | 5 | thien-2-yl-CH=CH— | |
| 50 | cyclo-C$_3$H$_5$ | 5 | thien-2-yl-CH=CH— | |
| 51 | 4-Cl—C$_6$H$_4$ | 5 | thien-2-yl-CH=CH— | |
| 52 | 4-OCH$_3$—C$_6$H$_4$ | 5 | thien-2-yl-CH=CH— | |
| 53 | (CH$_3$)$_2$CH | 5 | thien-2-yl-CH$_2$—CH$_2$— | |
| 54 | cyclo-C$_3$H$_5$ | 5 | thien-2-yl-CH$_2$—CH$_2$— | |
| 55 | 4-Cl—C$_6$H$_4$ | 5 | thien-2-yl-CH$_2$—CH$_2$— | |
| 56 | 4-OCH$_3$—C$_6$H$_4$ | 5 | thien-2-yl-CH$_2$—CH$_2$— | |
| 57 | (CH$_3$)$_2$CH | 5 | thien-2-yl-CH$_2$—O— | |
| 58 | cyclo-C$_3$H$_5$ | 5 | thien-2-yl-CH$_2$—O— | |

TABLE 1-continued

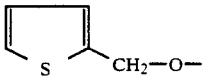

Compounds of the general formula I.
The first configuration statement refers to the methyl β-methoxyacrylate group, and the second to the ethenylene group in the compounds of the general formula I a (A = ethenylene).

| No. | R | Position of R on Het | Het—A— | mp.: (°C.) (Isomer) |
|---|---|---|---|---|
| 59 | 4-Cl—C$_6$H$_4$ | 5 | 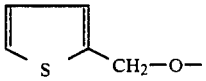 | |
| 60 | 4-OCH$_3$—C$_6$H$_4$ | 5 | 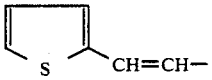 | |
| 61 | (CH$_3$)$_2$CH | 4 | 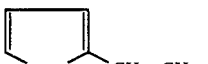 | |
| 62 | cyclo-C$_3$H$_5$ | 4 | 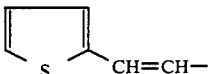 | |
| 63 | 4-Cl—C$_6$H$_4$ | 4 | 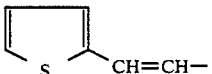 | |
| 64 | 4-OCH$_3$—C$_6$H$_4$ | 4 | 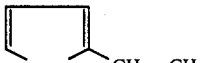 | |
| 65 | (CH$_3$)$_2$CH | 4 | 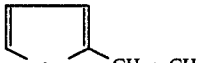 | |
| 66 | cyclo-C$_3$H$_5$ | 4 | 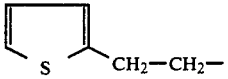 | |
| 67 | 4-Cl—C$_6$H$_4$ | 4 | 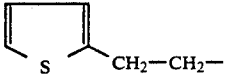 | |
| 68 | 4-OCH$_3$—C$_6$H$_4$ | 4 |  | |
| 69 | (CH$_3$)$_2$CH | 4 | 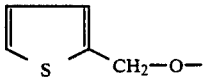 | |
| 70 | cyclo-C$_3$H$_5$ | 4 | | |

TABLE 1-continued

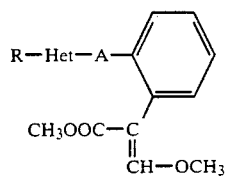
(I)

Compounds of the general formula I.
The first configuration statement refers to the methyl β-methoxyacrylate group, and the second to the ethenylene group in the compounds of the general formula I a (A = ethenylene).

| No. | R | Position of R on Het | Het—A— | mp.: (°C.) (Isomer) |
|-----|---|---|---|---|
| 71 | 4-Cl—C$_6$H$_4$ | 4 | thiophene-CH$_2$—O— | |
| 72 | 4-OCH$_3$—C$_6$H$_4$ | 4 | thiophene-CH$_2$—O— | |
| 73 | (CH$_3$)$_2$CH | 5 | thiophene-CH=CH— | |
| 74 | cyclo-C$_3$H$_5$ | 5 | thiophene-CH=CH— | |
| 75 | 4-Cl—C$_6$H$_4$ | 5 | thiophene-CH=CH— | |
| 76 | 4-OCH$_3$—C$_6$H$_4$ | 5 | thiophene-CH=CH— | |
| 77 | (CH$_3$)$_2$CH | 5 | thiophene-CH$_2$—CH$_2$— | |
| 78 | cyclo-C$_3$H$_5$ | 5 | thiophene-CH$_2$—CH$_2$— | |
| 79 | 4-Cl—C$_6$H$_4$ | 5 | thiophene-CH$_2$—CH$_2$— | |
| 80 | 4-OCH$_3$—C$_6$H$_4$ | 5 | thiophene-CH$_2$—CH$_2$— | |
| 81 | (CH$_3$)$_2$CH | 5 | thiophene-CH$_2$—O— | |

TABLE 1-continued (I)

R—Het—A—C₆H₄(—C(COOCH₃)=CH—OCH₃)

Compounds of the general formula I.
The first configuration statement refers to the methyl β-methoxyacrylate group, and the second to the ethenylene group in the compounds of the general formula I a (A = ethenylene).

| No. | R | Position of R on Het | Het—A— | mp.: (°C.) (Isomer) |
|---|---|---|---|---|
| 82 | cyclo-C₃H₅ | 5 | thiophene-CH₂—O— | |
| 83 | 4-Cl—C₆H₄ | 5 | thiophene-CH₂—O— | |
| 84 | 4-OCH₃—C₆H₄ | 5 | thiophene-CH₂—O— | |
| 85 | C₆H₅ | 1 | pyrazole-CH=CH— | |
| 86 | 4-CH₃—C₆H₄ | 1 | pyrazole-CH=CH— | 120–122 (E, E) |
| 87 | 4-Cl—C₆H₄ | 1 | pyrazole-CH=CH— | 141–143 (E, E) |
| 88 | 4-OCH₃—C₆H₄ | 1 | pyrazole-CH=CH— | |
| 89 | C₆H₅ | 1 | pyrazole-CH₂—CH₂— | |
| 90 | 4-CH₃—C₆H₄ | 1 | pyrazole-CH₂—CH₂— | |
| 91 | 4-Cl—C₆H₄ | 1 | pyrazole-CH₂—CH₂— | |
| 92 | 4-OCH₃—C₆H₄ | 1 | pyrazole-CH₂—CH₂— | |

TABLE 1-continued

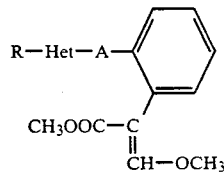

(I)

Compounds of the general formula I.
The first configuration statement refers to the methyl β-methoxyacrylate group, and the second to the ethenylene group in the compounds of the general formula I a (A = ethenylene).

| No. | R | Position of R on Het | Het—A— | mp.: (°C.) (Isomer) |
|---|---|---|---|---|
| 93 | C$_6$H$_5$ | 1 | pyrazole-CH$_2$—O— | |
| 94 | 4-CH$_3$—C$_6$H$_4$ | 1 | pyrazole-CH$_2$—O— | |
| 95 | 4-Cl—C$_6$H$_4$ | 1 | pyrazole-CH$_2$—O— | |
| 96 | 4-OCH$_3$—C$_6$H$_4$ | 1 | pyrazole-CH$_2$—O— | |
| 97 | C$_6$H$_5$ | 5 | N-methylpyrazole-CH=CH— | |
| 98 | cyclo-C$_3$H$_5$ | 5 | N-methylpyrazole-CH=CH— | |
| 99 | 4-Cl—C$_6$H$_4$ | 5 | N-methylpyrazole-CH=CH— | |
| 100 | 4-OCH$_3$—C$_6$H$_4$ | 5 | N-methylpyrazole-CH=CH— | |
| 101 | (CH$_3$)$_2$CH | 5 | N-methylpyrazole-CH$_2$—CH$_2$— | |

TABLE 1-continued

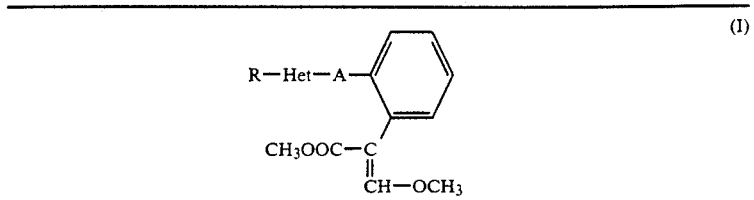

(I)

Compounds of the general formula I.
The first configuration statement refers to the methyl β-methoxyacrylate group, and the second to the ethenylene group in the compounds of the general formula I a (A = ethenylene).

| No. | R | Position of R on Het | Het—A— | mp.: (°C.) (Isomer) |
|---|---|---|---|---|
| 102 | cyclo-C$_3$H$_5$ | 5 | pyrazole-N-CH$_3$, CH$_2$—CH$_2$— | |
| 103 | 4-Cl—C$_6$H$_4$ | 5 | pyrazole-N-CH$_3$, CH$_2$—CH$_2$— | |
| 104 | 4-OCH$_3$—C$_6$H$_4$ | 5 | pyrazole-N-CH$_3$, CH$_2$—CH$_2$— | |
| 105 | (CH$_3$)$_2$CH | 5 | pyrazole-N-CH$_3$, CH$_2$—O— | |
| 106 | cyclo-C$_3$H$_5$ | 5 | pyrazole-N-CH$_3$, CH$_2$—O— | |
| 107 | 4-Cl—C$_6$H$_4$ | 5· | pyrazole-N-CH$_3$, CH$_2$—O— | |
| 108 | 4-OCH$_3$—C$_6$H$_4$ | 5 | pyrazole-N-CH$_3$, CH$_2$—O— | |
| 109 | C$_6$H$_5$ | 1 | imidazole, CH=CH— | |

TABLE 1-continued

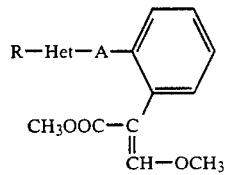

(I)

Compounds of the general formula I.
The first configuration statement refers to the methyl β-methoxyacrylate group, and the second to the ethenylene group in the compounds of the general formula I a (A = ethenylene).

| No. | R | Position of R on Het | Het—A— | mp.: (°C.) (Isomer) |
|---|---|---|---|---|
| 110 | 4-CH₃—C₆H₄ | 1 | pyrimidinyl-CH=CH— | |
| 111 | 4-Cl—C₆H₄ | 1 | pyrimidinyl-CH=CH— | |
| 112 | 4-OCH₃—C₆H₄ | 1 | pyrimidinyl-CH=CH— | |
| 113 | C₆H₅ | 1 | pyrimidinyl-CH₂—CH₂— | |
| 114 | 4-CH₃—C₆H₄ | 1 | pyrimidinyl-CH₂—CH₂— | |
| 115 | 4-Cl—C₆H₄ | 1 | pyrimidinyl-CH₂—CH₂— | |
| 116 | 4-OCH₃—C₆H₄ | 1 | pyrimidinyl-CH₂—CH₂— | |
| 117 | C₆H₅ | 1 | pyrimidinyl-CH₂—O— | |
| 118 | 4-CH₃—C₆H₄ | 1 | pyrimidinyl-CH₂—O— | |
| 119 | 4-Cl—C₆H₄ | 1 | pyrimidinyl-CH₂—O— | |
| 120 | 4-OCH₃—C₆H₄ | 1 | pyrimidinyl-CH₂—O— | |

TABLE 1-continued

Compounds of the general formula I.
The first configuration statement refers to the methyl β-methoxyacrylate group, and the second to the ethenylene group in the compounds of the general formula I a (A = ethenylene).

| No. | R | Position of R on Het | Het—A— | mp.: (°C.) (Isomer) |
|---|---|---|---|---|
| 121 | $(CH_3)_2CH$ | 3 | isoxazole-CH=CH— | 90-91 (E, E) |
| 122 | cyclo-$C_3H_5$ | 3 | isoxazole-CH=CH— | 109-111 (E, E) |
| 123 | 4-Cl—$C_6H_4$ | 3 | isoxazole-CH=CH— | 161-163 (E, E) |
| 124 | 4-OCH$_3$—$C_6H_4$ | 3 | isoxazole-CH=CH— | 130-132 (E, E) |
| 125 | 4-CH$_3$—$C_6H_4$ | 3 | isoxazole-CH=CH— | 138-140 (E, E) |
| 126 | 4-CN—$C_6H_4$ | 3 | isoxazole-CH=CH— | 163-165 (E, E) |
| 127 | 2,6-$F_2$—$C_6H_3$ | 3 | isoxazole-CH=CH— | 126-128 (E, E) |
| 128 | $CO_2C_2H_5$ | 3 | isoxazole-CH=CH— | |
| 129 | $(CH_3)_2CH$ | 3 | isoxazole-CH$_2$—CH$_2$— | |
| 130 | cyclo-$C_3H_5$ | 3 | isoxazole-CH$_2$—CH$_2$— | |
| 131 | 4-Cl—$C_6H_4$ | 3 | isoxazole-CH$_2$—CH$_2$— | |
| 132 | 4-OCH$_3$—$C_6H_4$ | 3 | isoxazole-CH$_2$—CH$_2$— | |

TABLE 1-continued

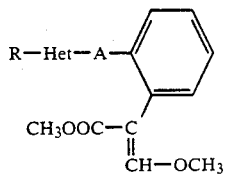

(I)

Compounds of the general formula I.
The first configuration statement refers to the methyl β-methoxyacrylate group, and the second to the ethenylene group in the compounds of the general formula I a (A = ethenylene).

| No. | R | Position of R on Het | Het—A— | mp.: (°C.) (Isomer) |
|-----|---|---|---|---|
| 133 | 4-CH$_3$—C$_6$H$_4$ | 3 | isoxazolyl-CH$_2$—CH$_2$— | |
| 134 | 4-CN—C$_6$H$_4$ | 3 | isoxazolyl-CH$_2$—CH$_2$— | |
| 135 | 2,6-F$_2$—C$_6$—H$_4$ | 3 | isoxazolyl-CH$_2$—CH$_2$— | |
| 136 | CO$_2$C$_2$H$_5$ | 3 | isoxazolyl-CH$_2$—CH$_2$— | |
| 137 | (CH$_3$)$_2$CH | 3 | isoxazolyl-CH$_2$—O— | |
| 138 | cyclo-C$_3$H$_5$ | 3 | isoxazolyl-CH$_2$—O— | |
| 139 | 4-Cl—C$_6$H$_4$ | 3 | isoxazolyl-CH$_2$—O— | |
| 140 | 4-OCH$_3$—C$_6$H$_4$ | 3 | isoxazolyl-CH$_2$—O— | |
| 141 | 4-CH$_3$—C$_6$H$_4$ | 3 | isoxazolyl-CH$_2$—O— | |
| 142 | 4-CN—C$_6$H$_4$ | 3 | isoxazolyl-CH$_2$—O— | |
| 143 | 2,6-F$_2$—C$_6$H$_4$ | 3 | isoxazolyl-CH$_2$—O— | |
| 144 | CO$_2$C$_2$H$_5$ | 3 | isoxazolyl-CH$_2$—O— | |

TABLE 1-continued

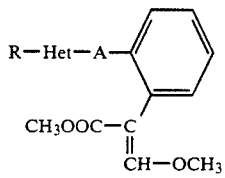

Compounds of the general formula I.
The first configuration statement refers to the methyl β-methoxyacrylate group, and the second to the ethenylene group in the compounds of the general formula I a (A = ethenylene).

| No. | R | Position of R on Het | Het—A— | mp.: (°C.) (Isomer) |
|-----|---|---|---|---|
| 145 | $(CH_3)_2CH$ | 5 | isoxazole-CH=CH— | |
| 146 | cyclo-$C_3H_5$ | 5 | isoxazole-CH=CH— | |
| 147 | 4-Cl—$C_6H_4$ | 5 | isoxazole-CH=CH— | |
| 148 | 4-OCH$_3$—$C_6H_4$ | 5 | isoxazole-CH=CH— | |
| 149 | $(CH_3)_2CH$ | 5 | isoxazole-CH$_2$—CH$_2$ | |
| 150 | cyclo-$C_3H_5$ | 5 | isoxazole-CH$_2$—CH$_2$ | |
| 151 | 4-Cl—$C_6H_4$ | 5 | isoxazole-CH$_2$—CH$_2$ | |
| 152 | 4-OCH$_3$—$C_6H_4$ | 5 | isoxazole-CH$_2$—CH$_2$ | |
| 153 | $(CH_3)_2CH$ | 5 | isoxazole-CH$_2$—CH$_2$ | |
| 154 | cyclo-$C_3H_5$ | 5 | isoxazole-CH$_2$—O— | |
| 155 | 4-Cl—$C_6H_4$ | 5 | isoxazole-CH$_2$—O— | |

TABLE 1-continued

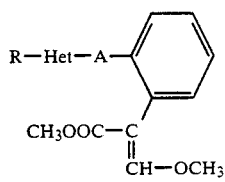
(I)

Compounds of the general formula I.
The first configuration statement refers to the methyl β-methoxyacrylate group, and the second to the ethenylene group in the compounds of the general formula I a (A = ethenylene).

| No. | R | Position of R on Het | Het—A— | mp.: (°C.) (Isomer) |
|---|---|---|---|---|
| 156 | 4-OCH$_3$—C$_6$H$_4$ | 5 | isoxazole-CH$_2$—O— | |
| 157 | (CH$_3$)$_2$CH | 3 | thiazole-CH=CH— | |
| 158 | cyclo-C$_3$H$_5$ | 3 | thiazole-CH=CH— | |
| 159 | 4-Cl—C$_6$H$_4$ | 3 | thiazole-CH=CH— | |
| 160 | 4-OCH$_3$—C$_6$H$_4$ | 3 | thiazole-CH=CH— | |
| 161 | (CH$_3$)$_2$CH | 3 | thiazole-CH$_2$—CH$_2$ | |
| 162 | cyclo-C$_3$H$_5$ | 3 | thiazole-CH$_2$—CH$_2$ | |
| 163 | 4-Cl—C$_6$H$_4$ | 3 | thiazole-CH$_2$—CH$_2$ | |
| 164 | 4-OCH$_3$—C$_6$H$_4$ | 3 | thiazole-CH$_2$—CH$_2$ | |
| 165 | (CH$_3$)$_2$CH | 3 | thiazole-CH$_2$—O— | |
| 166 | cyclo-C$_3$H$_5$ | 3 | thiazole-CH$_2$—O— | |
| 167 | 4-Cl—C$_6$H$_4$ | 3 | thiazole-CH$_2$—O— | |

TABLE 1-continued

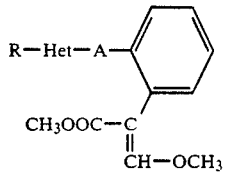

(I)

Compounds of the general formula I.
The first configuration statement refers to the methyl β-methoxyacrylate group, and the second to the ethenylene group in the compounds of the general formula I a (A = ethenylene).

| No. | R | Position of R on Het | Het—A— | mp.: (°C.) (Isomer) |
|---|---|---|---|---|
| 168 | 4-OCH₃—C₆H₄ | 3 | isothiazole-CH₂—O— | |
| 169 | (CH₃)₂CH | 2 | oxazole-CH=CH— | |
| 170 | cyclo-C₃H₅ | 2 | oxazole-CH=CH— | |
| 171 | 4-Cl—C₆H₄ | 2 | oxazole-CH=CH— | |
| 172 | 4-OCH₃—C₆H₄ | 2 | oxazole-CH=CH— | |
| 173 | (CH₃)₂CH | 2 | oxazole-CH₂—CH₂ | |
| 174 | cyclo-C₃H₅ | 2 | oxazole-CH₂—CH₂ | |
| 175 | 4-Cl—C₆H₄ | 2 | oxazole-CH₂—CH₂ | |
| 176 | 4-OCH₃—C₆H₄ | 2 | oxazole-CH₂—CH₂ | |
| 177 | (CH₃)₂CH | 2 | oxazole-CH₂—O— | |
| 178 | cyclo-C₃H₅ | 2 | oxazole-CH₂—O— | |

TABLE 1-continued $$\text{R-Het-A-} \underset{\underset{\text{CH-OCH}_3}{\|}}{\overset{\text{CH}_3\text{OOC-C}}{}} \text{-C}_6\text{H}_4 \quad (I)$$

Compounds of the general formula I.
The first configuration statement refers to the methyl β-methoxyacrylate group, and the second to the ethenylene group in the compounds of the general formula I a (A = ethenylene).

| No. | R | Position of R on Het | Het—A— | mp.: (°C.) (Isomer) |
|-----|---|---|---|---|
| 179 | 4-Cl—C$_6$H$_4$ | 2 | oxazol-2-yl, CH$_2$—O— | |
| 180 | 4-OCH$_3$—C$_6$H$_4$ | 2 | oxazol-2-yl, CH$_2$—O— | |
| 181 | (CH$_3$)$_2$CH | 2 | thiazol-2-yl, CH=CH— | |
| 182 | Cyclo-C$_3$H$_5$ | 2 | thiazol-2-yl, CH=CH— | |
| 183 | 4-Cl—C$_6$H$_4$ | 2 | thiazol-2-yl, CH=CH— | |
| 184 | 4-OCH$_3$—C$_6$H$_4$ | 2 | thiazol-2-yl, CH=CH— | |
| 185 | (CH$_3$)$_2$CH | 2 | thiazol-2-yl, CH$_2$—CH$_2$ | |
| 186 | cyclo-C$_3$H$_5$ | 2 | thiazol-2-yl, CH$_2$—CH$_2$ | |
| 187 | 4-Cl—C$_6$H$_4$ | 2 | thiazol-2-yl, CH$_2$—CH$_2$ | |
| 188 | 4-OCH$_3$—C$_6$H$_4$ | 2 | thiazol-2-yl, CH$_2$—CH$_2$ | |

TABLE 1-continued $$R-Het-A-\underset{\underset{CH-OCH_3}{\parallel}}{\overset{CH_3OOC-C}{\bigg|}}\text{—}\bigg\langle\!\!\!\bigcirc\!\!\!\bigg\rangle$$ (I)

Compounds of the general formula I.
The first configuration statement refers to the methyl β-methoxyacrylate group, and the second to the ethenylene group in the compounds of the general formula I a (A = ethenylene).

| No. | R | Position of R on Het | Het—A— | mp.: (°C.) (Isomer) |
|---|---|---|---|---|
| 189 | (CH$_3$)$_2$CH | 2 | 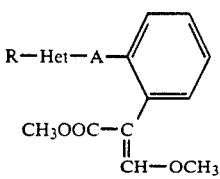 | |
| 190 | cyclo-C$_3$H$_5$ | 2 | 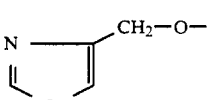 | |
| 191 | 4-Cl—C$_6$H$_4$ | 2 | 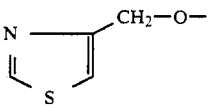 | |
| 192 | 4-OCH$_3$—C$_6$H$_4$ | 2 | 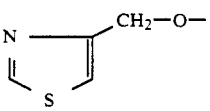 | |
| 193 | (CH$_3$)$_2$CH | 3 | 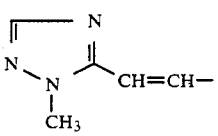 | |
| 194 | cyclo-C$_3$H$_5$ | 3 | 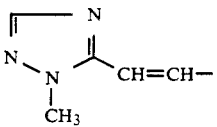 | |
| 195 | 4-Cl—C$_6$H$_4$ | 3 | 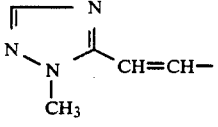 | |
| 196 | 4-OCH$_3$—C$_6$H$_4$ | 3 | 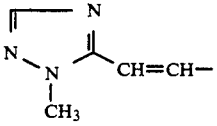 | |
| 197 | (CH$_3$)$_2$CH | 3 | 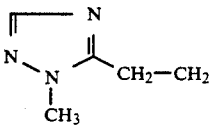 | |
| 198 | cyclo-C$_3$H$_5$ | 3 | 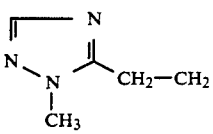 | |

TABLE 1-continued

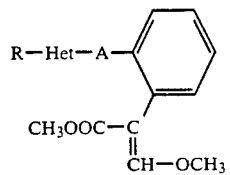
(I)

Compounds of the general formula I.
The first configuration statement refers to the methyl β-methoxyacrylate group, and the second to the ethenylene group in the compounds of the general formula I a (A = ethenylene).

| No. | R | Position of R on Het | Het—A— | mp.: (°C.) (Isomer) |
|---|---|---|---|---|
| 199 | 4-Cl—C$_6$H$_4$ | 3 | N=N, N(CH$_3$), CH$_2$—CH$_2$ | |
| 200 | 4-OCH$_3$—C$_6$H$_4$ | 3 | N=N, N(CH$_3$), CH$_2$—CH$_2$ | |
| 201 | (CH$_3$)$_2$CH | 3 | N=N, N(CH$_3$), CH$_2$—O— | |
| 202 | cyclo-C$_3$H$_5$ | 3 | N=N, N(CH$_3$), CH$_2$—O— | |
| 203 | 4-Cl—C$_6$H$_4$ | 3 | N=N, N(CH$_3$), CH$_2$—O— | |
| 204 | 4-OCH$_3$—C$_6$H$_4$ | 3 | N=N, N(CH$_3$), CH$_2$—O— | |
| 205 | (CH$_3$)$_2$CH | 5 | N—N, O, CH=CH— | 91–92 (E, E) |
| 206 | cyclo-C$_3$H$_5$ | 5 | N—N, O, CH=CH— | |
| 207 | 4-Cl—C$_6$H$_4$ | 5 | N—N, O, CH=CH— | |
| 208 | 4-OCH$_3$—C$_6$H$_4$ | 5 | N—N, O, CH=CH— | |

TABLE 1-continued $$\text{R—Het—A—}\underset{\underset{\text{CH—OCH}_3}{\|}}{\overset{\text{CH}_3\text{OOC—C}}{\phantom{X}}}\text{—(phenyl)} \tag{I}$$

Compounds of the general formula I.
The first configuration statement refers to the methyl β-methoxyacrylate group, and the second to the ethenylene group in the compounds of the general formula I a (A = ethenylene).

| No. | R | Position of R on Het | Het—A— | mp.: (°C.) (Isomer) |
|---|---|---|---|---|
| 209 | (CH₃)₂CH | 5 | N—N, O, CH₂—CH₂ (oxadiazole) | |
| 210 | cyclo-C₃H₅ | 5 | N—N, O, CH₂—CH₂ | |
| 211 | 4-Cl—C₆H₄ | 5 | N—N, O, CH₂—CH₂ | |
| 212 | 4-OCH₃—C₆H₄ | 5 | N—N, O, CH₂—CH₂ | |
| 213 | (CH₃)₂CH | 5 | N—N, O, CH₂—O— | |
| 214 | cyclo-C₃H₅ | 5 | N—N, O, CH₂—O— | |
| 215 | 4-Cl—C₆H₄ | 5 | N—N, O, CH₂—O— | |
| 216 | 4-OCH₃—C₆H₄ | 5 | N—N, O, CH₂—O— | |
| 217 | (CH₃)₂CH | 5 | N—N, S, CH=CH— | |
| 218 | cyclo-C₃H₅ | 5 | N—N, S, CH=CH— | |
| 219 | C₂H₅O | 5 | N—N, S, CH=CH— | |
| 220 | 4-Cl—C₆H₄ | 5 | N—N, S, CH=CH— | 152-153 (E,E) |

TABLE 1-continued

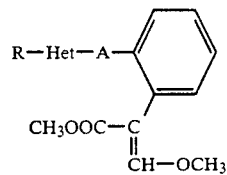

Compounds of the general formula I.
The first configuration statement refers to the methyl β-methoxyacrylate group, and the second to the ethenylene group in the compounds of the general formula I a (A = ethenylene).

| No. | R | Position of R on Het | Het—A— | mp.: (°C.) (Isomer) |
|---|---|---|---|---|
| 221 | 4-OCH$_3$—C$_6$H$_4$ | 5 | N=N, S, —C(=)—CH=CH— | |
| 222 | (CH$_3$)$_2$CH | 5 | N=N, S, —C(=)—CH$_2$—CH$_2$ | |
| 223 | cyclo-C$_3$H$_5$ | 5 | N=N, S, —C(=)—CH$_2$—CH$_2$ | |
| 224 | C$_2$H$_5$O | 5 | N=N, S, —C(=)—CH$_2$—CH$_2$ | |
| 225 | 4-Cl—C$_6$H$_4$ | 5 | N=N, S, —C(=)—CH$_2$—CH$_2$ | |
| 226 | 4-OCH$_3$—C$_6$H$_4$ | 5 | N=N, S, —C(=)—CH$_2$—CH$_2$ | |
| 227 | (CH$_3$)$_2$CH | 5 | N=N, S, —C(=)—CH$_2$—O— | |
| 228 | cyclo-C$_3$H$_5$ | 5 | N=N, S, —C(=)—CH$_2$—O— | |
| 229 | C$_2$H$_5$O— | 5 | N=N, S, —C(=)—CH$_2$—O— | |
| 230 | 4-Cl—C$_6$H$_4$ | 5 | N=N, S, —C(=)—CH$_2$—O— | |
| 231 | 4-OCH$_3$—C$_6$H$_4$ | 5 | N=N, S, —C(=)—CH$_2$—O— | |
| 232 | (CH$_3$)$_2$CH | 5 | N, O, N, —C(=)—CH=CH— | |

TABLE 1-continued $$\text{R—Het—A—}\underset{\underset{\overset{\|}{CH-OCH_3}}{CH_3OOC-C}}{C_6H_4}\quad (I)$$

Compounds of the general formula I.
The first configuration statement refers to the methyl β-methoxyacrylate group, and the second to the ethenylene group in the compounds of the general formula I a (A = ethenylene).

| No. | R | Position of R on Het | Het—A— | mp.: (°C.) (Isomer) |
|---|---|---|---|---|
| 233 | cyclo-C$_3$H$_5$ | 5 | isoxazole-CH=CH— | |
| 234 | 4-Cl—C$_6$H$_4$ | 5 | isoxazole-CH=CH— | |
| 235 | 4-OCH$_3$—C$_6$H$_4$ | 5 | isoxazole-CH=CH— | |
| 236 | (CH$_3$)$_2$CH | 5 | isoxazole-CH$_2$—CH$_2$— | |
| 237 | cyclo-C$_3$H$_5$ | 5 | isoxazole-CH$_2$—CH$_2$— | |
| 238 | 4-Cl—C$_6$H$_4$ | 5 | isoxazole-CH$_2$—CH$_2$— | |
| 239 | 4-OCH$_3$—C$_6$H$_4$ | 5 | isoxazole-CH$_2$—CH$_2$— | |
| 240 | (CH$_3$)$_2$CH | 5 | isoxazole-CH$_2$—O— | |
| 241 | cyclo-C$_3$H$_5$ | 5 | isoxazole-CH$_2$—O— | |
| 242 | 4-Cl—C$_6$H$_4$ | 5 | isoxazole-CH$_2$—O— | |
| 243 | 4-OCH$_3$—C$_6$H$_4$ | 5 | isoxazole-CH$_2$—O— | |

TABLE 1-continued $$R-Het-A-\underset{\underset{CH-OCH_3}{\parallel}}{\underset{C}{CH_3OOC-}}\text{-phenyl}$$ (I)

Compounds of the general formula I.
The first configuration statement refers to the methyl β-methoxyacrylate group, and the second to the ethenylene group in the compounds of the general formula I a (A = ethenylene).

| No. | R | Position of R on Het | Het—A— | mp.: (°C.) (Isomer) |
|---|---|---|---|---|
| 244 | (CH₃)₂CH | 3 | oxadiazole-CH=CH— | |
| 245 | cyclo-C₃H₅ | 3 | oxadiazole-CH=CH— | |
| 246 | 4-Cl—C₆H₄ | 3 | oxadiazole-CH=CH— | 111–113 (E, E) |
| 247 | 4-OCH₃—C₆H₄ | 3 | oxadiazole-CH=CH— | |
| 248 | (CH₃)₂CH | 3 | oxadiazole-CH₂—CH₂ | |
| 249 | cyclo-C₃H₅ | 3 | oxadiazole-CH₂—CH₂ | |
| 250 | 4-Cl—C₆H₄ | 3 | oxadiazole-CH₂—CH₂ | |
| 251 | 4-OCH₃—C₆H₄ | 3 | oxadiazole-CH₂—CH₂ | |
| 252 | (CH₃)₂CH | 3 | oxadiazole-CH₂—O— | |
| 253 | cyclo-C₃H₅ | 3 | oxadiazole-CH₂—O— | |
| 254 | 4-Cl—C₆H₄ | 3 | oxadiazole-CH₂—O— | |
| 255 | 4-OCH₃—C₆H₄ | 3 | oxadiazole-CH₂—O— | |

TABLE 1-continued

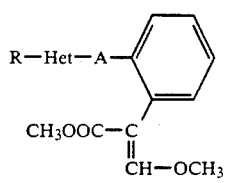

(I)

Compounds of the general formula I.
The first configuration statement refers to the methyl β-methoxyacrylate group, and the second to the ethenylene group in the compounds of the general formula I a (A = ethenylene).

| No. | R | Position of R on Het | Het—A— | mp.: (°C.) (Isomer) |
|-----|---|----------------------|--------|---------------------|
| 256 | (CH₃)₂CH | 3 | thiadiazole-CH=CH— | |
| 257 | cyclo-C₃H₅ | 3 | thiadiazole-CH=CH— | |
| 258 | 4-Cl—C₆H₄ | 3 | thiadiazole-CH=CH— | |
| 259 | 4-OCH₃—C₆H₄ | 3 | thiadiazole-CH=CH— | |
| 260 | (CH₃)₂CH | 3 | thiadiazole-CH₂—CH₂ | |
| 261 | cyclo-C₃H₅ | 3 | thiadiazole-CH₂—CH₂ | |
| 262 | 4-Cl—C₆H₄ | 3 | thiadiazole-CH₂—CH₂ | |
| 263 | 4-OCH₃—C₆H₄ | 3 | thiadiazole-CH₂—CH₂ | |
| 264 | (CH₃)₂CH | 3 | thiadiazole-CH₂—O— | |
| 265 | cyclo-C₃H₅ | 3 | thiadiazole-CH₂—O— | |
| 266 | 4-Cl—C₆H₄ | 3 | thiadiazole-CH₂—O— | |
| 267 | 4-OCH₃—C₆H₄ | 3 | thiadiazole-CH₂—O— | |

TABLE 1-continued

Compounds of the general formula I.
The first configuration statement refers to the methyl β-methoxyacrylate group, and the second to the ethenylene group in the compounds of the general formula I a (A = ethenylene).

| No. | R | Position of R on Het | Het—A— | mp.: (°C.) (Isomer) |
|---|---|---|---|---|
| 268 | 2-F—C$_6$H$_4$ | 1 | 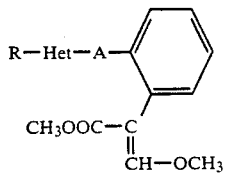 | 91–92 (E, E) |
| 269 | 3-F—C$_6$H$_4$ | 1 |  | 138–139 (E, E) |
| 270 | 4-F—C$_6$H$_4$ | 1 |  | 138 (E, E) |
| 271 | 3-Cl—C$_6$H$_4$ | 1 |  | 141–142 (E, E) |
| 272 | 4-CH$_3$—C$_6$H$_4$ | 1 |  | 124–125 (E, E) |
| 273 | 4-t-C$_4$H$_9$—C$_6$H$_4$ | 1 |  | 105–106 (E, E) |
| 274 | 2,6-F$_2$—C$_6$H$_3$ | 1 |  | 116–117 (E, E) |
| 275 | 3,4-Cl$_2$—C$_6$H$_3$ | 1 |  | 147–149 (E, E) |
| 276 | 4-F—C$_6$H$_4$ | 1 |  | 115–117 (E, E) |
| 277 | 4-Br—C$_6$H$_4$ | 1 |  | 138–140 (E, E) |
| 278 | CH$_3$ | 3 |  | 155–157 (E, E) |

TABLE 1-continued

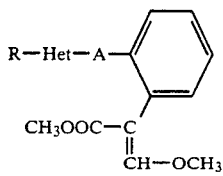

(I)

Compounds of the general formula I.
The first configuration statement refers to the methyl β-methoxyacrylate group, and the second to the ethenylene group in the compounds of the general formula I a (A = ethenylene).

| No. | R | Position of R on Het | Het—A— | mp.: (°C.) (Isomer) |
|---|---|---|---|---|
| 279 | $C_6H_5$ | 3 | (isoxazole, CH=CH—) | 117-119 (E, E) |
| 280 | 2-Cl-6-F—$C_6H_3$ | 3 | (isoxazole, CH=CH—) | oil (E, E) |
| 281 | $CH_3$ | 3 | (isoxazole, $CH_2$—O—) | oil (E, E) |
| 282 | 4-$CH_3$—$C_6H_4$ | 5 | (oxadiazole, CH=CH—) | 147 (E, E) |
| 283 | $C_6H_5$ | 5 | (oxadiazole, CH=CH—) | 144 (E, E) |

TABLE 2

NMR data of selected compounds from Table 1. The chemical shift (δ) is given in ppm relative to tetramethylsilane. $CDCl_3$ was used as solvent.

Compound no. 8
3.70(s, 3H); 3.80(s, 3H); 6.53(d, 1H); 6.80(d, 1H); 6.95(d, 1H); 7.00(d, 1H); 7.10(s, 1H); 7.15-7.70(m, 8H); 7.63(s, 1H).

Compound no. 14
2.78(m, 4H); 3.73(s, 3H); 3.86(s, 3H); 6.21(d, 1H); 6.82(s, 1H); 6.98(d, 1H); 7.11-7.42(m, 8H); 7.63(s, 1H).

Compound no. 122
0.82(m, 2H); 1.00(m, 2H); 2.00(m, 1H); 3.68(s, 3H); 3.80(s, 3H); 5.88(s, 1H); 6.84(d, 1H); 7.17-7.68(m, 4H); 7.28(d, 1H); 7.65(s, 1H).

Compound no. 123
3.70(s, 3H); 3.82(s, 3H); 6.50(s, 1H); 6.92(d, 1H); 7.19-7.79(m, 9H); 7.68(s, 1H).

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia species in cotton and lawns,
Ustilago species in cereals and sugar cane,
Venturia inaequalis (scab) in apples,
Helminthosporium species in cereals,
Septoria nodorum in wheat,
Botrytis cinerea (gray mold) in strawberries and grapes,
Cercospora arachidicola in groundnuts,
Pseudocercosporella herpotrichoides in wheat and barley,
Pyricularia oryzae in rice,
Phytophthora infestans in potatoes and tomatoes,
Fusarium and Verticillium species in various plants,
Plasmopara viticola in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicidal agents generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, for example against Paecilomyces variotii.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 8 is mixed with 10 parts by weight of N-methyl-α-pyrrolidone. A mixture is obtained which is suitable for application in the form of very fine drops.

II. 20 parts by weight of compound no. 14 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 122 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 8 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 14 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 122 is intimately mixed with 97 parts by weight of particulate kaolin. A dust is obtained containing 3% by weight of the active ingredient.

VII. 30 parts by weight of compound no. 8 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 14 is intimately mixed with 10 parts by weight of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 122 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

The following list of fungicides with which the novel compounds may be combined is intended to illustrate possible combinations but not to impose any restrictions. Examples of fungicides which may be combined with the novel compounds are:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebis(thiocarbamyl) disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
heterocyclic substances, such as
2-heptadecylimidazol-2-yl acetate,
2,4-dichloro-6-(o-chloroanilino)-s-triazine,
O,O-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole, N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenyl-sulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
1-(4-phenylphenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

Use Examples

For comparison purposes, the compound methyl α-2-(6-chloropyrazin-2-oxy)phenyl-β-methoxyacrylate (C) disclosed in EP-260, 794 was used.

Use Example 1

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of Plasmopara viticola. The plants were first placed for 48 hours in a water vaporsaturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results of this experiment show that active ingredients 14, 86, 87, 122, 123, 124, 125, 126, 220, 270, 276, 277, 278, 279 and 280, applied as 0.0125 wt % spray liquors, have a better fungicidal action (95%) than prior art comparative agent C (60%).

Use Example 2

Action on *Septoria nodorum*

Wheat plants of the "Frühgold" variety were sprayed to runoff at the one-leaf stage with aqueous formulations consisting (dry basis) of 80% of active ingredient and 20% of emulsifier. 20 hours after the sprayed-on layer had dried, the plants were inoculated with an aqueous spore suspension of Septoria nodorum until droplets formed, and placed for a week in a climatic cabinet at from 17° to 19° C. and a relative humidity of approx. 90 to 95%. The spread of the symptoms was then assessed.

The results of this experiment show that active ingredients 8, 14, 86, 87, 121, 205, 246, 268, 269, 272, 277, 280, 281 and 282, applied as 0.05 wt % spray liquors, have a very good fungicidal action (95%).

Use Example 3

Action on *Pyrenophora teres*

Barley seedlings of the "Igri" variety were sprayed to runoff at the two-leaf stage with aqueous suspensions consisting (dry basis) of 80% of active ingredient and 20% of emulsifier. After 24 hours the plants were inoculated with a spore suspension of the fungus Pyrenophora teres, and set up for 48 hours in a high-humidity climatic cabinet at 18° C. The plants were then cultivated for a further 5 days in the greenhouse at 20° to 22°

C. and a relative humidity of 70° C. The extent of fungus spread was then assessed.

The results of this experiment show that active ingredients 86, 87, 125, 126, 205, 246, 276, 277, 278 and 280, applied as 0.0125 wt % spray liquors, have a better fungicidal action (95%) than prior art active ingredient C (55%).

The novel compounds are also suitable for effectively combating pests from the class of insects, mites and nematodes. They may be used as pesticides in crop protection, and in the hygiene, stores protection and veterinary sectors.

Examples of injurious insects from the Lepidoptera order are *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grndiosella, Earias insulana, Elasmopalpus lignosellus, Eupoecilia ambiguella, Evetria bouliana, Feltia subterranea, Galleria mellonella, Grapholita funebrana, Grapholita molesta, Heliothis armigera, Heliothis virescens, Heliothis zea, Hellula undalis, Hibernia defoliaria, Hyphantria cunea, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flamea, Pectinophora gossypiella, Peridroma saucia, Phalera bucephala, Phthorimaea operculella, Phyllocnistis citrella, Pieris brassicae, Plathypena scarbra, Plutella xylostella, Pseudoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis.*

Examples from the Coleoptera order are *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus* and *Sitophilus granaria.*

Examples from the Diptera order are *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa.*

Examples from the Thysanoptera order are *Frankliniella fusca, Frankliniella occidentalis, Frankliniella tritici, Scirtothrips citri, Thrips oryzae, Thrips palmi* and *Thrips tabaci.*

Examples from the Hymenoptera order are *Athalia rosae, Atta cephalotes, Atta sexdens, Atta texana, Hoplocampa minuta, Hoplocampa testudinea, Monomorium pharaonis, Solenopsis geminata* and *Solenopsis invicta.*

Examples from the Heteroptera order are *Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis* and *Thyanta perditor.*

Examples from the nematode class are root-knot nematodes, e.g., *Meloidogyne hapla, Meloidogyne incognita* and *Meloidogyne javanica,* cyst-forming nematodes, e.g., *Globodera rostochiensis, Heterodera avenae, Hetrodera glycinae, Heterodera schatii, Hetrodera triflolii,* stem and leaf eelworms, e.g., *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Paratylenchus curvitatus, Partylenchus goodeyi.*

For combating pests, the active ingredient concentrations in the finished formulations may vary over a wide range. Generally, they are from 0.0001 to 10, and preferably from 0.001 to 0.1, %.

The active ingredients may also successfully be used in the ultra-low-volume (ULV) method, where it is possible to apply formulations containing more than 95 wt % of active ingredient, or even the active ingredient without additives.

In the open, the amount of active ingredient applied is for example from 0.01 to 10, particularly from 0.1 to 1.0, kg/ha. For comparison purposes, the compounds 2-($\beta$-methoxy-$\alpha$-methoxycarbonylvinyl)-4'-chlorostilbene (A) and methyl $\alpha$-[2-(benzoxazol-2'-yloxy)-phenyl]-$\beta$-methoxyacrylate (B) disclosed in EP 178,826 and EP 256,667 were used.

Use Example 4

*Prodenia litura*

Type of experiment: Effect of ingested food

The experiment was carried out in 250 ml plastic beakers. Two caterpillars were placed in each vessel, and pieces of Indian corn plants which had been previously dipped for 5 seconds into aqueous formulations of the active ingredients were proffered as food. The amount of active ingredient is given in ppm. The kill rate was assessed in % after 24 hours.

| Active ingredient no. | Prodenia | |
| --- | --- | --- |
| | ppm | Kill rate (%) |
| 8 | 40 | 100 |

-continued

| Active ingredient no. | Prodenia | |
|---|---|---|
| | ppm | Kill rate (%) |
| 123 | 200 | 80 |
| A | 1000 | 0 |
| B | 1000 | 80 |

Use Example 5

*Musca domestica*

Type of experiment: Continuous contact action

Both tops and bottoms of a glass dish 10 cm in diameter were wetted with a total of 1 ml of acetonic solutions of the active ingredients. The amount of active ingredient is given in ppm. After the solvent had evaporated, 10 flies were introduced into each dish, each dish was closed and the animals in supine position were counted after 4 hours and the kill rate was determined in %.

| Active ingredient no. | Musca | |
|---|---|---|
| | ppm | Kill rate (%) |
| 8 | 2 | 100 |
| 14 | 2 | 100 |
| A | 2 | 0 |
| B | 4 | 80 |

Use Example 6

*Plutella maculipennis*

Type of experiment: Contact action

Young cabbage leaves were dipped for 3 seconds into aqueous formulations of the candidate compounds (amount of active ingredient in ppm) and placed in a glass dish (10 cm in diameter) on a circular filter paper (9 cm in diameter) moistened with 0.5 ml of water. 10 caterpillars of the fourth larval stage were then placed on each leaf and the dishes were closed. The kill rate was assessed in % after 48 hours.

| Active ingredient no. | Plutella | |
|---|---|---|
| | ppm | Kill rate (%) |
| 8 | 100 | 100 |
| 14 | 1000 | 100 |
| 123 | 200 | 100 |
| A | 1000 | 0 |
| B | 200 | 0 |
| | 1000 | 80 |

Use Example 7

*Ornithodorus moubata*

Type of experiment: Contact action

Yound ticks (1.5 to 2 mm in diameter) which had sucked blood once were individually picked up by means of a suction tube. A strong light source drove the active animals from the discarded exoskeleton remains.

5 ticks were placed in paper bags, and the bags were dipped for 5 seconds in aqueous active ingredient formulations (amounts of active ingredient given in ppm). The bags were then suspended and the action was assessed after 48 hours by holding the bags up to a strong light source (60 watt bulb); the animals still living attempted to escape and were easy to recognize from their movements. The temperature was kept at about 25° C. The kill rate was determined in %.

| Active ingredient no. | Ticks | |
|---|---|---|
| | ppm | Kill rate (%) |
| 8 | 400 | 80 |
| 14 | 1000 | 0 |
| 121 | 1000 | 80 |
| 125 | 1000 | 60 |
| 279 | 1000 | 60 |
| A | 1000 | 0 |
| B | 1000 | 0 |

Use Example 8

*Tetranychus telarius*; contact action; spray experiment

Potted bush beans exhibiting the first pair of leaves were sprayed to runoff with aqueous formulations of the active ingredients. The plants were sprayed from all sides with a total of 50 ml of spray liquor. The plants were under heavy mite attack and numerous eggs had been laid on them.

The action was assessed after 5 days by means of a binocular magnifying glass, care being taken to ascertain whether animals of all development stages were killed. For the 5 days of the experiment, the plants were subjected to normal greenhouse conditions.

| Active ingredient no. | ppm | Kill rate (%) |
|---|---|---|
| 121 | 100 | 100 |
| 125 | 40 | 80 |
| 126 | 400 | 100 |
| 279 | 100 | 100 |
| B | 1000 | 0 |

We claim:

1. Methyl α-arylacrylates substituted by a heterocyclic radical and having the general formula $$R-Het-A-\underset{\underset{CH-OCH_3}{\parallel}}{\overset{}{\underset{}{C}}}\text{(aromatic ring)} \quad (I)$$

CH$_3$OOC—C(=CH—OCH$_3$)— where R is $C_1$–$C_8$-alkyl, $C_2$–$C_8$-alkenyl, $C_1$–$C_4$-haloalkyl, $C_3$–$C_6$-cycloalkyl, $C_1$–$C_4$-alkoxy, $C_1$–$C_4$-alkylcarbonyl, $C_1$–$C_4$-alkoxycarbonyl, halogen or phenyl, the aromatic ring being unsubstituted or substituted by $C_1$–$C_8$-alkyl, $C_3$–$C_6$-cycloalkyl, $C_1$–$C_2$-haloalkyl, $C_1$–$C_4$-alkoxy, halogen, cyano or nitro, Het is pyrazolyl which is unsubstituted or substituted by methyl at a nitrogen atom and is bonded to A via a carbon atom, and A is ethenylene, ethylene, methyleneoxy or methylenethio.

2. A compound as set forth in claim 1, where R is fluorophenyl in the 1-position, Het is pyrazol and A is ethenylene.

3. A compound as set forth in claim 1, where R is bromophenyl in the 1-position, Het is pyrazolyl and A is ethenylene.

4. A fungicide containing an inert carrier and a fungicidally effective amount of a methyl α-arylacrylate substituted by a heterocyclic radical and having the general formula

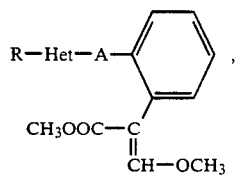

where R is $C_1$–$C_8$-alkyl, $C_2$–$C_8$-alkenyl, $C_1$–$C_4$-haloalkyl, $C_3$–$C_6$-cycloalkyl, $C_1$–$C_4$-alkoxy, $C_1$–$C_4$-alkylcarbonyl, $C_1$–$C_4$-alkoxycarbonyl, halogen of phenyl, the aromatic ring being unsubstituted or substituted by $C_1$–$C_8$-alkyl, $C_3$–$C_6$-cycloalkyl, $C_1$–$C_2$-haloalkyl, $C_1$–$C_4$-alkoxy, halogen, cyano or nitro, Het is pyrazolyl which is unsubstituted or substituted by methyl at a nitrogen atom and is bonded to A via a carbon atom, and A is ethenylene, ethylene, methyleneoxy or methylenethio.

5. A process for combating fungi, wherein the fungi, or the materials, plants, seed or the soil are treated with a fungicidally effective amount of a methyl α-arylacrylate substituted by a heterocyclic radical and having the general formula

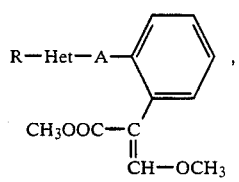

where R is $C_1$–$C_8$-alkyl, $C_2$–$C_8$-alkenyl, $C_1$–$C_4$-haloalkyl, $C_3$–$C_6$-cycloalkyl, $C_1$–$C_4$-alkoxy, $C_1$–$C_4$-alkylcarbonyl, $C_1$–$C_4$-alkoxycarbonyl, halogen or phenyl, the aromatic ring being unsubstituted or substituted by $C_1$–$C_8$-alkyl, $C_3$–$C_6$-cycloalkyl, $C_1$–$C_2$-haloalkyl, $C_1$–$C_4$-alkoxy, halogen, cyano or nitro, Het is pyrazolyl which is unsubstituted or substituted by methyl at a nitrogen atom and is bonded to A via a carbon atom, and A is ethenylene, ethylene, methyleneoxy or methylenethio.

6. An insecticide containing an inert carrier and an insecticidally effective amount of a methyl α-arylacrylate substituted by a heterocyclic radical and having the general formula

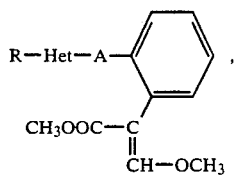

where R is $C_1$–$C_8$-alkyl, $C_2$–$C_8$-alkenyl, $C_1$–$C_4$-haloalkyl, $C_3$–$C_6$-cycloalkyl, $C_1$–$C_4$-alkoxy, $C_1$–$C_4$-alkylcarbonyl, $C_1$–$C_4$-alkoxycarbonyl, halogen or phenyl, the aromatic ring being unsubstituted or substituted by $C_1$–$C_8$-alkyl, $C_3$–$C_6$-cycloalkyl, $C_1$–$C_2$-haloalkyl, $C_1$–$C_4$-alkoxy, halogen, cyano or nitro, Het is pyrazolyl which is unsubstituted or substituted by methyl at a nitrogen atom and is bonded to A via a carbon atom, and A is ethenylene, ethylene, methyleneoxy or methylenethio.

7. A process for combating insects, mites and nemotodes, wherein an insecticidally effective amount of a methyl α-arylacrylate substituted by a heterocyclic radical and having the general formula

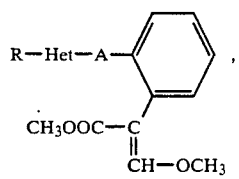

where R is $C_1$–$C_8$-alkyl, $C_2$–$C_8$-alkenyl, $C_1$–$C_4$-haloalkyl, $C_3$–$C_6$-cycloalkyl, $C_1$–$C_4$-alkoxy, $C_1$–$C_4$-alkylcarbonyl, $C_1$–$C_4$-alkoxycarbonyl, halogen or phenyl, the aromatic ring being unsubstituted or substituted by $C_1$–$C_8$-alkyl, $C_3$–$C_6$-cycloalkyl, $C_1$–$C_2$-haloalkyl, $C_1$–$C_4$-alkoxy, halogen, cyano or nitro, Het is pyrazolyl which is unsubstituted or substituted by methyl at a nitrogen atom and is bonded to A via a carbon atom, and A is ethenylene, ethylene, methyleneoxy or methylenethio, is allowed to act on the pests or their habitat.

* * * * *